(12) United States Patent
Bousquet et al.

(10) Patent No.: US 8,299,785 B2
(45) Date of Patent: Oct. 30, 2012

(54) DEVICE FOR THE NON-DESTRUCTIVE TESTING OF PARTS IN A TURBOMACHINE

(75) Inventors: Sadia Bousquet, Moissy Cramayel (FR); Patrick Gaisnon, Cannes Ecluse (FR); Sylvie Mozer, Sivry Courtry (FR); Nicolas Samak, Dammarie les Lys (FR)

(73) Assignee: SNECMA, Paris (FR)

( * ) Notice: Subject to any disclaimer, the term of this patent is extended or adjusted under 35 U.S.C. 154(b) by 210 days.

(21) Appl. No.: 12/831,576

(22) Filed: Jul. 7, 2010

(65) Prior Publication Data

US 2011/0018530 A1    Jan. 27, 2011

(30) Foreign Application Priority Data

Jul. 9, 2009  (FR) ...................... 09 03398

(51) Int. Cl.
*G01N 27/72* (2006.01)
*G01N 27/82* (2006.01)

(52) U.S. Cl. ........................ 324/220; 324/240
(58) Field of Classification Search ................ None
See application file for complete search history.

(56) References Cited

U.S. PATENT DOCUMENTS

| 4,139,822 | A | * | 2/1979 | Urich et al. ................. 324/219 |
| 4,628,207 | A | | 12/1986 | Elfert et al. |
| 2007/0223643 | A1 | | 9/2007 | Yamane et al. |
| 2009/0058441 | A1 | * | 3/2009 | Hirakawa et al. ........... 324/754 |

FOREIGN PATENT DOCUMENTS

| DE | 27 33 862 A1 | 2/1979 |
| DE | 197 48 795 A1 | 5/1998 |
| EP | 2 042 076 A2 | 4/2009 |

OTHER PUBLICATIONS

U.S. Appl. No. 13/377,429, filed Dec. 9, 2011, Gaisnon, et al.

\* cited by examiner

*Primary Examiner* — Roberto Velez
(74) *Attorney, Agent, or Firm* — Oblon, Spivak, McClelland, Maier & Neustadt, L.L.P.

(57) ABSTRACT

A device for the non-destructive testing of parts of a turbomachine motor, including a longitudinal rod carrying at its distal end a longitudinal finger carrying a retractile or deployable flexible blade supporting an inspection probe, this blade being guided in axial translation on the finger between a retracted position in which it extends along the finger and an advanced or deployed position in which it extends in front of the finger.

13 Claims, 3 Drawing Sheets

DEVICE FOR THE NON-DESTRUCTIVE TESTING OF PARTS IN A TURBOMACHINE

The present invention concerns a device for the non-destructive testing of parts of a motor, in particular of a turbomachine.

BACKGROUND OF THE INVENTION

Non-destructive testing (NDT) of parts of a turbomachine motor makes it possible to check the state of these parts without damaging them. In some cases, this testing may require the motor to be removed and partly dismantled in order to inspect parts that are difficult to access with the inspection means.

A known inspection device comprises a rigid rod carrying a test probe or sensor at its distal end. Where the turbomachine is equipped with endoscopic orifices, this rod is introduced into the turbomachine through one of these orifices for the in situ inspection of parts of the turbomachine, which avoids removing the motor.

However, the area accessible to this rod is very limited and in general extends in line with the endoscopic orifice and at a short distance from this orifice. In addition, when the probe carried by the rod must be used on a part to be inspected, this probe must be applied with a certain pressure and for a given period on a surface of this part, which is not always possible with the aforementioned device.

For example, in the case of a turbomachine comprising seals of the labyrinth type, each of these seals comprises external annular lips carried by the rotor of the turbomachine and cooperating with blocks of abradable material carried by an internal annular platform of stator blades of the turbomachine. To access the lips of a labyrinth seal, the inspection probe must be passed through a very narrow space, which may have a width or axial dimension of approximately 1 mm, which is not possible with the aforementioned rod.

As a result some areas of a turbomachine remain difficult to access with the known non-destructive testing devices, since these are not designed to pass through orifices or passages of small size and through several orifices and/or non-aligned consecutive passages.

SUMMARY OF THE INVENTION

The invention proposes a simple, effective and economical solution to the problems of the prior art.

The subject matter thereof is in particular a non-destructive testing device for inspecting parts whatever their position and accessibility in a turbomachine.

To this end it proposes a device for the non-destructive testing of parts of a motor, in particular a turbomachine, comprising a longitudinal rod at the distal end of which an inspection probe is mounted, characterised in that the rod carries at its distal end a longitudinal finger carrying a retractile or deployable flexible blade supporting the inspection probe, this blade being guided in axial translation on the finger between a retracted position in which it extends along the finger and an advanced or deployed position in which it extends at least in front of the finger.

In this device, the blade that carries the inspection probe is configured so as to be introduced into very narrow spaces, in order to position the probe in places that are difficult to access in the turbomachine. The blade is relatively thin and may have a thickness less than or equal to approximately 1 mm. At rest it preferably has an elongate and slightly curved shape around its elongation axis. The blade according to the invention is advantageously elastically deformable in flexion, which makes it possible in particular to apply the probe with a certain pressure (corresponding to the elastic return force of the blade) on the surface of the part to be inspected, when this probe must be in abutment on the part during inspection. The support blade of the probe is also retractile or deployable on the finger between a retracted position in which it extends along and alongside the finger and a deployed or advanced position in which it extends in front of the finger. The blade is brought into the retracted position prior to the introduction of the rod in the turbomachine in order to protect the probe against any impacts with surrounding parts.

According to another feature of the invention, the finger is mounted so as to pivot by one of its ends on the distal end of the rod, about an axis substantially perpendicular to the longitudinal axis of the rod. This makes it possible to increase further the areas accessible to the device according to the invention. The pivoting of the finger can be controlled by a rigid or semi-rigid cable extending along the rod and connected at its distal end to the finger. In the present application, semi-rigid cable means a cable that is slightly deformable in flexion.

Advantageously, the blade is fixed by one of its ends to a ring that the finger passes through and that is mounted so as to slide axially on this finger. The movement in translation of the blade can be controlled by a rigid or semi-rigid cable extending along the rod and connected at its distal end to the ring.

The aforementioned cables can be housed inside the rod and be connected to appropriate control means situated at the proximal end of the rod.

The inspection probe may be fixed, for example by adhesive bonding, to a free end of the blade. By way of example, the inspection probe is an eddy current sensor.

According to yet another feature of the invention, the blade is removably fixed to the finger or to the ring, which makes it possible in particular to replace the blade and therefore the probe when the latter is worn or when the probe or other particular type must be replaced by a probe of another type.

The device according to the invention can also comprise an optical observation channel extending along the rod and emerging at its distal end in the vicinity of the distal end of the rod. This makes it possible to visually inspect a part or the surroundings of a part during inspection thereof by means of the probe, or to facilitate the movement and positioning of the rod in the endoscope orifices or the passages of the turbomachine.

The rod can carry at its distal end a non-slip damping shoe which, when a part is being inspected, is intended to come into abutment on an element of the motor in order to stabilise the device.

BRIEF DESCRIPTION OF THE DRAWINGS

The invention will be better understood and other details, features and advantages of the present invention will emerge more clearly from a reading of the following description, given by way of non-limitative examples and with reference to the accompanying drawings, in which.

MORE DETAILED DESCRIPTION

Figure 1:
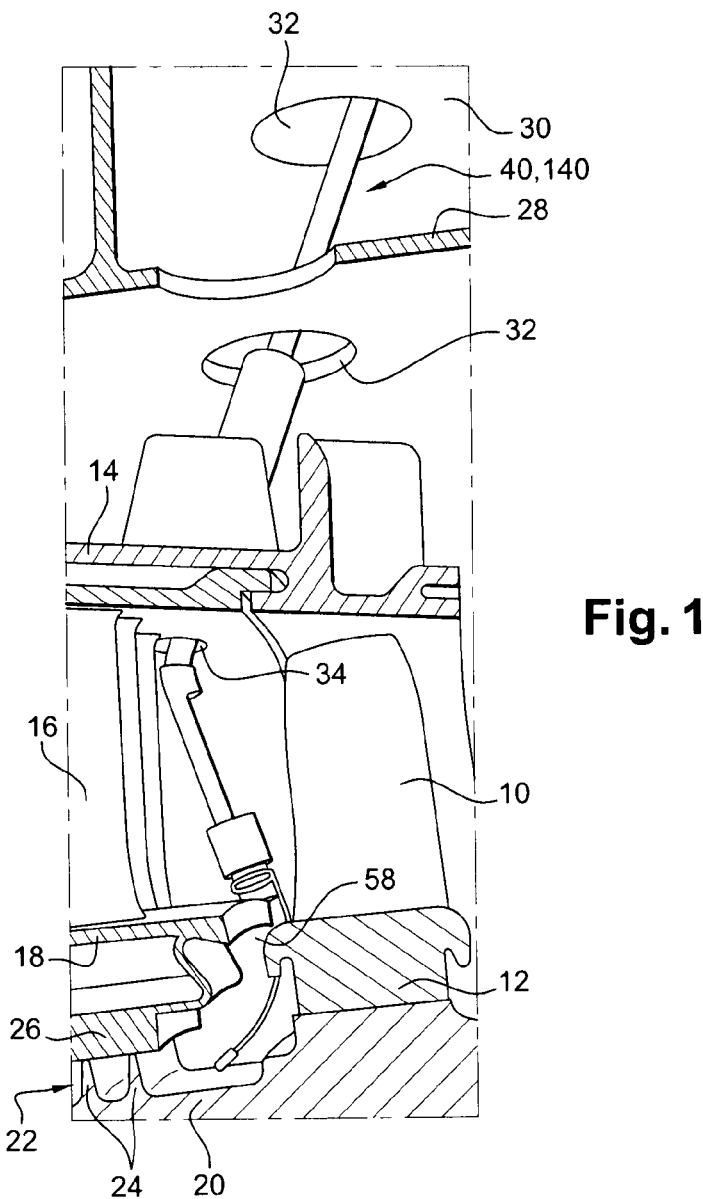
FIG. 1 is a schematic view in axial section of a part of a turbomachine comprising endoscopic orifices for an inspection device according to the invention to pass.

Reference is made first of all to FIG. 1, which shows schematically a part of a turbomachine, in particular a turbine or compressor stage of this turbomachine.

This turbine or compressor stage comprises an annular row of rotor blades 10 carried by a disc 12 and rotating inside a substantially cylindrical wall 14, and an annular row of stator blades 16 disposed upstream of the rotor blades 10 and carried at their radially external ends by the wall 14. The stator blades 16 are connected at their radially internal ends to an annular platform 18, this platform 18 and the external periphery of the disc 12 delimiting with the wall 14 the gas flow stream in the turbomachine.

The platform 18 surrounds a substantially cylindrical rotor wall 20 connecting the rotor disc 12 to another rotor disc (not visible) situated upstream of the stator blades 16.

A seal of the labyrinth type is mounted between the rotor wall 20 and the platform 18, and comprises annular lips 24 extending radially towards the outside from the rotor wall 20 and engaging with blocks of an abradable material 26 fixed to the internal periphery of the platform 18.

The wall 14 is surrounded by a double-wall casing 28, 30 that comprises endoscopic orifices 32 for passage of a device 40 for the in situ inspection according to the invention of parts that are difficult to access, such as the rotor wall 20 and the annular lips 24.

Figure 2:
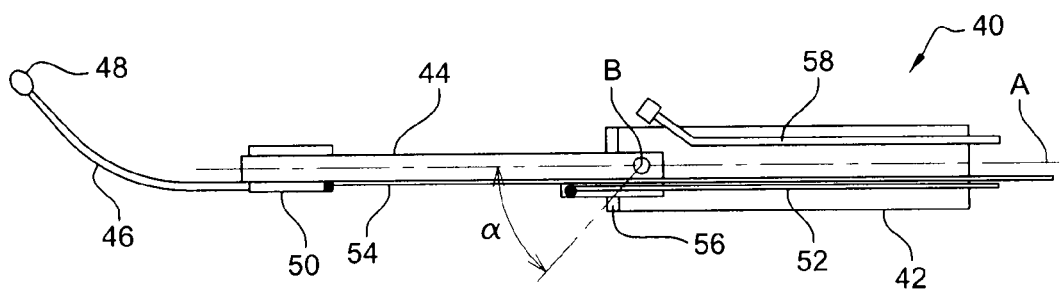
FIG. 2 is a highly schematic partial view in axial section of the device in FIG. 1.
Figure 3:
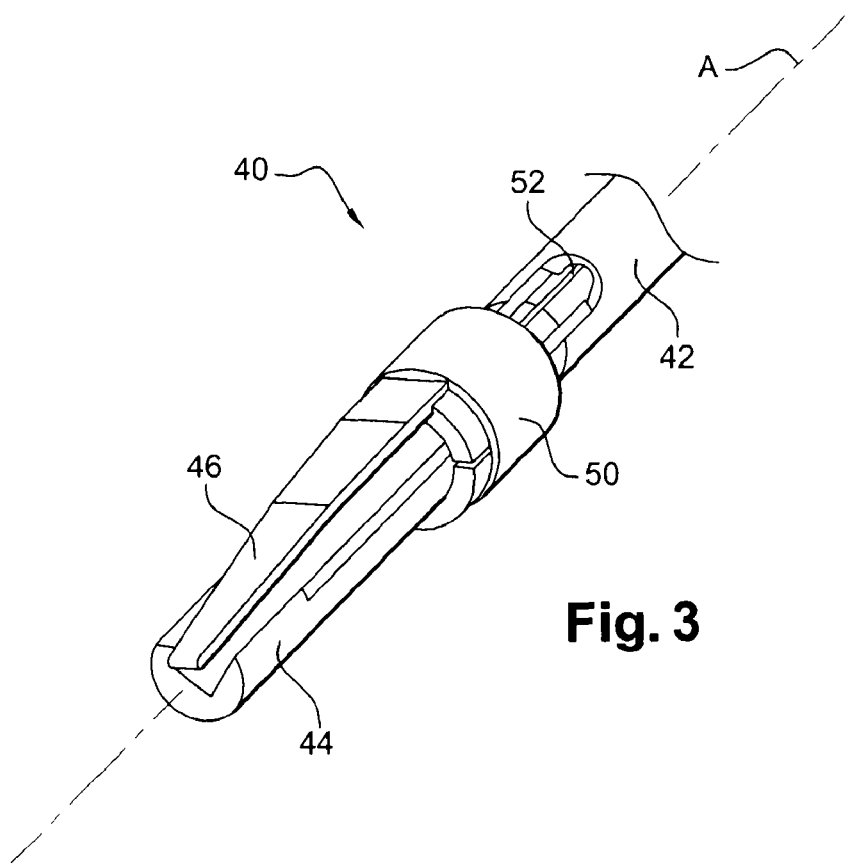
FIGS. 3 and 4 are partial schematic views in perspective of the device in FIG. 1, and show two different positions of the support blade of the inspection probe according to the invention.
Figure 4:
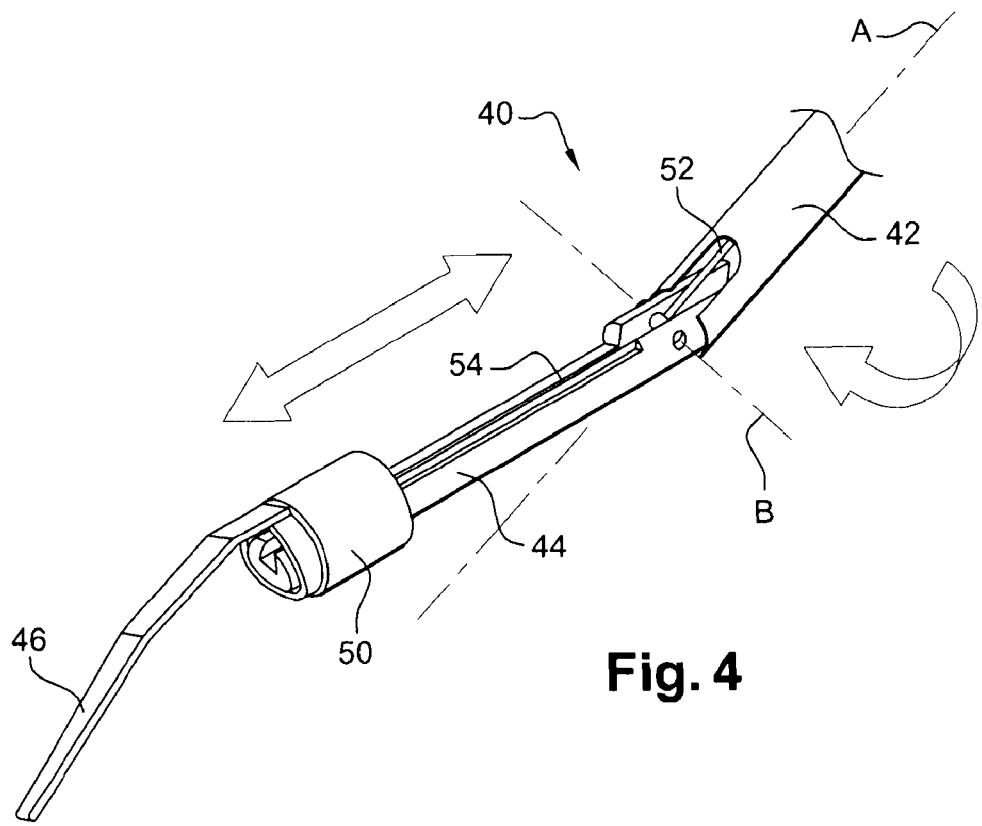

The device 40 according to the invention, more clearly visible in FIGS. 2 to 4, comprises a rigid longitudinal rod 42 carrying at its distal end a pivoting finger 44 on which a flexible and retractile blade 46 supporting an inspection probe 48 or sensor is mounted so as to slide axially.

The finger 44 has an elongate shape and is mounted so as to pivot by one of its ends on the distal end of the rod 42, about an axis B perpendicular to the longitudinal axis A of the rod. The finger 44 is able to be moved about this axis B between a position shown in FIGS. 2 and 3 in which it extends along the axis A of the rod and a position shown in FIGS. 1 and 4 in which it is inclined with respect to this axis. The finger 44 pivots about the axis B over an angle α of approximately 45° (FIG. 2).

The blade 46 has an elongate shape, its longitudinal axis extending substantially along the axis of the finger 44. The blade is also curved about an axis perpendicular to its longitudinal axis. The blade is elastically deformable in flexion so as in particular to modify its curvature. It has a small thickness that is less than or equal to approximately 1 mm.

The control sensor 48 is fixed, for example by adhesive bonding, to the free end of the blade 46. The blade 46 is fixed removably or not by its other end to a ring 50 that is mounted so as to slide axially on the finger 44 between a rear position shown in FIG. 3 and a forward position shown in FIGS. 1, 2 and 4.

In the example shown, the blade 46 is fixed to the front annular edge of the ring 50 and its free end is intended to be situated in the vicinity of the free end of the finger 44 when the ring is in the rearward position on the finger (FIG. 3). In this position, the blade is in the retracted position. When the ring 50 is in the forward position on the finger (FIG. 4), the blade is deployed and extends in front of the finger 44.

The curvature of the blade is oriented so that the device forms substantially an S when the finger 44 is inclined with respect to the axis A of the rod 42 and the blade 46 is deployed (FIGS. 1 and 4).

The movement in translation of the ring 50 on the finger 44 and the pivoting of the finger are controlled remotely, from the proximal end of the rod 42, by means of cables 52, 54 or the like extending along the rod 42. These cables 52, 54 are advantageously housed inside the rod when the latter is tubular.

The cable 52 controlling the pivoting of the finger 44 is connected at its distal end in the vicinity of the proximal end of the finger, and the cable 54 controlling the movement of the ring 50 is connected at its distal end to the ring. The proximal ends of these cables 52, 54 are connected to appropriate control means situated at the proximal end of the rod 42.

These cables 52, 54 are of the "piano wire" type and sufficiently rigid to transmit a traction or thrust force, from the proximal end of the rod, as far as the finger 44 and the ring 50, respectively. They are however slightly deformable in flexion and their distal end parts are intended to adopt a slightly curved position when the finger is in an inclined position with respect to the axis A.

The ring 50 can also be mounted removably on the finger. The removable character of the mounting of the blade on the ring or of the ring on the finger enables the blade to be replaced by another blade, for example in the case of wear on the blade or probe or to change the type of probe with which the blade is equipped.

The probe 48 may be a sensor of the eddy current type. In this case, this probe must be applied with a certain pressure to a surface of the part to be inspected and for a given period. This is made possible by the fact that the blade is elastically deformable in flexion. This is because, when the device is in a position of inspecting a part, the free end of the blade carrying the probe is applied to the surface to be inspected and the blade is slightly deformed in flexion, this deformation causing an elastic return that ensures that the probe is put in abutment with a given pressure against the surface of the part to be inspected.

To immobilise the device according to the invention when the part is being inspected, the rod 42 comprises at its distal end a non-slip damping shoe 56 intended to be in abutment on an element of the turbomachine. This shoe can for example be produced from elastomer. In the case in FIG. 1, the shoe 56 bears on the edge of an endoscopic orifice 34 in the wall 14 through which the rod 42 passes.

To facilitate the positioning of the device in the turbomachine, the latter can also be equipped with an optical channel 58 extending along the rod 42, this optical channel 58 emerging at its distal end in the vicinity of the distal end of the rod and being connected at its proximal end to an eyepiece or a camera. The optical channel 58 can be formed by a cluster of optical fibres and/or a series of lenses.

Figure 5:
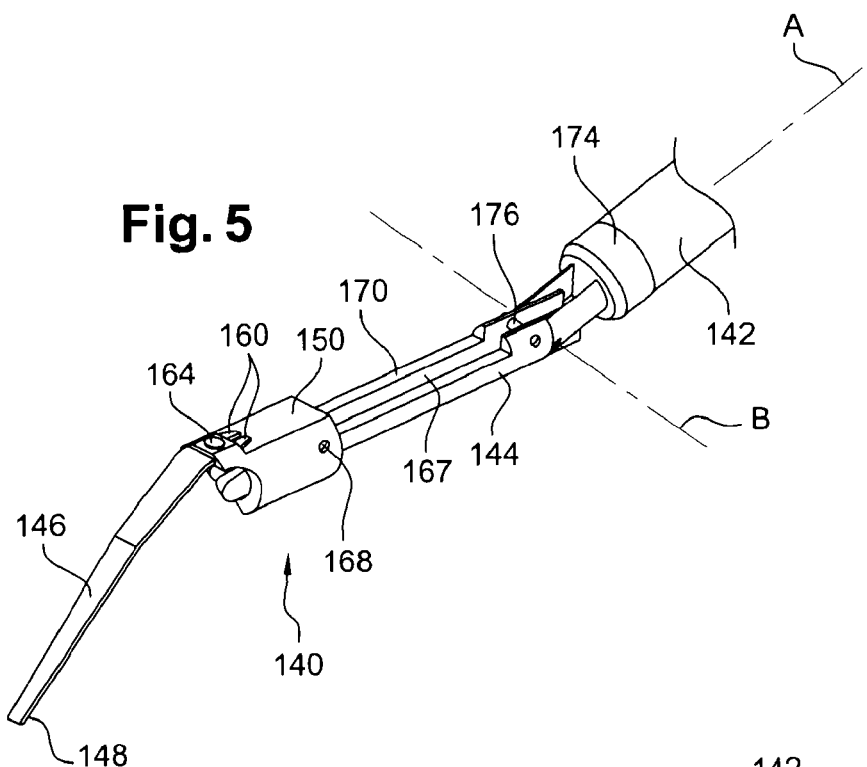
FIG. 5 is a partial schematic view in perspective of a variant embodiment of the device according to the invention.
Figure 6:
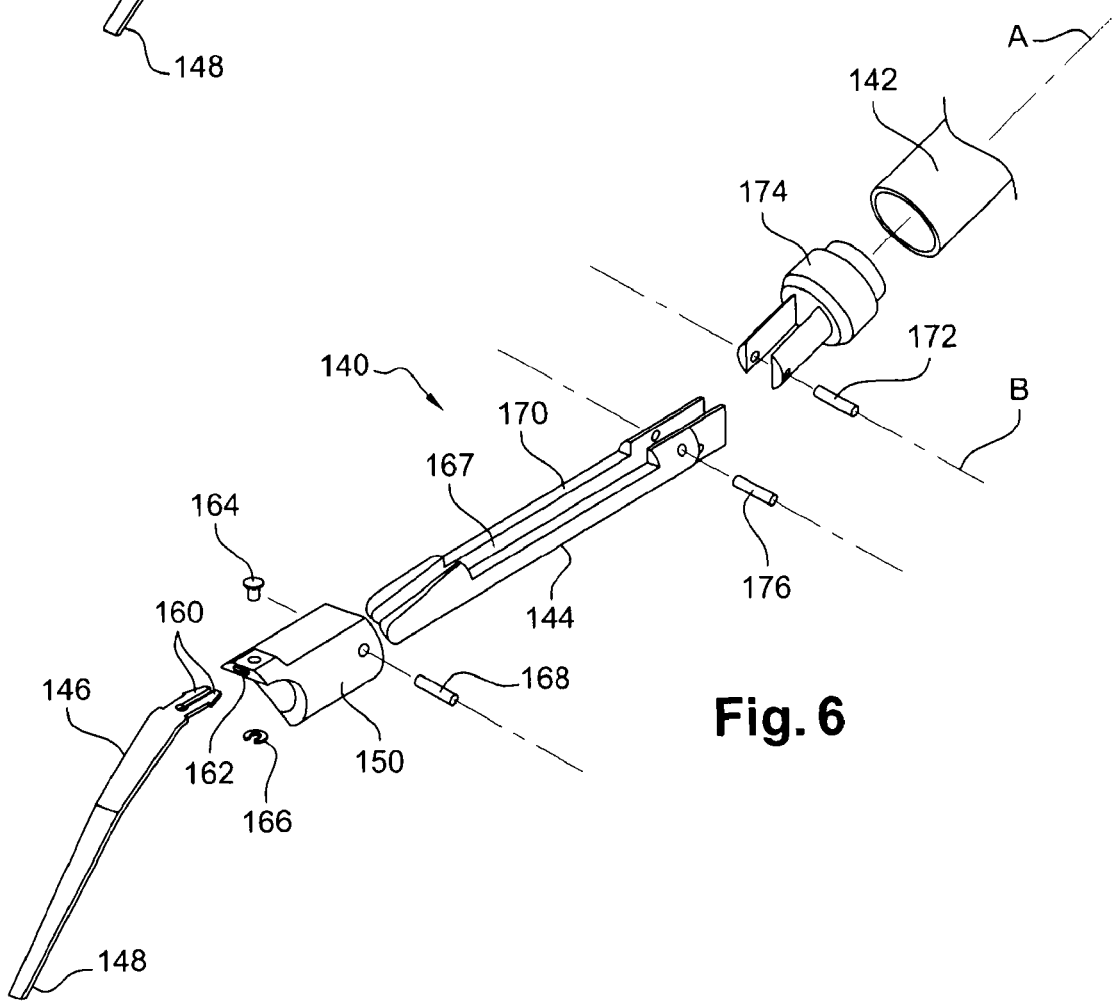
FIG. 6 is a schematic view in exploded perspective of the device in FIG. 5.

Reference is now made to FIGS. 5 and 6, which show a more detailed variant embodiment of the device 140 according to the invention, in which the blade 146 comprises, at its end opposite to the inspection probe 148, lugs 160 intended to be engaged in a slot 162 in the front end of the ring 150 and to cooperate by elastic snapping with this ring in order to ensure the removable mounting of the blade on the ring.

A cylindrical stud 164 is engaged in orifices in the front end of the ring 150 and passes through a corresponding orifice in the blade 146, situated between its two lugs 160, in order to lock the blade on the ring. This stud 164 comprises at one end a head bearing on a top face of the ring and receives at its opposite end means 166 of the circlip type, which bear on a bottom face of the ring.

The ring 150 is tubular and has passing through it axially the finger 144, which comprises a longitudinal groove 167 housing cables (not shown) controlling the movement of the ring and the pivoting of the finger.

The ring 150 carries at its rear end a cylindrical stem 168 extending perpendicular to the longitudinal axis of the finger 144 and intended to slide in a longitudinal notch 170 in the finger extending over a middle and top part of the finger in order to guide the ring in translation on the finger. The cable controlling the pivoting of the finger is connected at its distal end to the middle part of this stem 168.

The finger 144 is articulated at its proximal end on a spindle 172 carried by a connecting piece 174 fixed to the distal end of the rod 142, this spindle 172 defining the aforementioned pivot axis B of the finger. The connecting piece 174 carries a non-slip damping shoe 156 of the aforementioned type.

The finger 144 also carries, in the vicinity of its proximal end, a cylindrical stem 176 extending perpendicular to the longitudinal axis of the finger, and to the middle part of which the distal end of the cable controlling the pivoting of the finger is fixed.

The control of the rotor wall 20 of FIG. 1 by means of the device according to the invention is achieved as follows. The finger 44, 144 and the blade 46, 146 are brought into their positions shown in FIG. 3, that is to say the finger 44, 144 is aligned with the axis A of the rod 42, 142 and the blade 46, 146 is retracted and extends along the finger. The device 40, 140 is engaged in the orifices 32 in the double-wall casing 28, 30 and the orifice 34 of the wall 14, until the finger 44, 144 is situated in the gas flow stream of the compressor or turbine. The finger 44, 144 is then moved so as to pivot about the axis B over approximately 45° and the rod 42, 142 is turned about its axis A, so that the free end of the blade 46, 146 is situated at the annular space 58 between the downstream annular edge of the internal platform 18 of the stator blades 16 and the upstream annular edge of the disc 12 carrying the rotor blades 10. The blade 46, 146 is then deployed by moving the ring 50, 150 over the finger towards the front, until the inspection probe 48, 148 comes into abutment on the external surface of the rotor wall 20 carrying the annular lips 24. This causes a slight elastic deformation in flexion of the blade, the elastic return force of which holds the probe against the wall 20. The inspection of the wall 20 by means of the probe 48, 148 can then commence. The rotor wall 20 is moved in rotation about its axis so as to inspect a complete annular zone (extending over 360°) of this wall by means of the probe.

The invention claimed is:

1. A device for the non-destructive testing of parts of a motor, comprising a longitudinal rod at the distal end of which an inspection probe is mounted, wherein the rod carries at its distal end a longitudinal finger carrying a flexible blade supporting the inspection probe, said blade being movable in axial translation on the finger between a retracted position in which it extends along the finger and an advanced or deployed position in which it extends at least partly in front of the finger and the finger being mounted pivotally by one of its ends on the distal end of the rod, about an axis perpendicular to the longitudinal axis of the rod.

2. The device according to claim 1, wherein the blade is elastically deformable in flexion.

3. The device according to claim 1, wherein the pivoting of the finger is controlled by a rigid or semi-rigid cable extending along the rod and connected at its distal end to the finger.

4. The device according to claim 1, wherein the inspection probe is fixed at a free end of the blade.

5. The device according to claim 1, wherein the blade is fixed removably to the finger.

6. The device according to claim 1, wherein the blade has at rest an elongate shape curved about an axis perpendicular to its elongation axis.

7. The device according to claim 1, further comprising an optical observation channel extending along the rod and emerging at its distal end in the vicinity of the distal end of the rod.

8. The device according to claim 1, wherein the rod carries at its distal end a non-slip damping shoe which, when a part is being inspected, is intended to be in abutment on an element of the motor in order to stabilise the device.

9. The device according to claim 1, wherein the inspection probe is an eddy current sensor.

10. The device according to claim 1, wherein said device is configured to test parts in a turbomachine.

11. The device according to claim 1, wherein said blade has a thickness of less than or equal to approximately 1 mm.

12. A device for the non-destructive testing of parts of a motor, comprising a longitudinal rod at the distal end of which an inspection probe is mounted, wherein the rod carries at its distal end a longitudinal finger carrying a flexible blade supporting the inspection probe, said blade being movable in axial translation on the finger between a retracted position in which it extends along the finger and an advanced or deployed position in which it extends at least partly in front of the finger and the finger being mounted pivotally by one of its ends on the distal end of the rod, about an axis perpendicular to the longitudinal axis of the rod, and wherein the blade is fixed by one of its ends to a ring that the finger passes through and that is mounted so as to slide axially on this finger.

13. The device according to claim 12, wherein the translation movement of the blade on the finger is controlled by a rigid or semi-rigid cable extending along the rod and connected at its distal end to the ring.

* * * * *